(12) United States Patent
Ruchala et al.

(10) Patent No.: US 10,155,798 B2
(45) Date of Patent: Dec. 18, 2018

(54) ANTI-OBESITY COMPOUNDS DERIVED FROM NEUROMEDIN U

(71) Applicant: The Regents of the University of California, Oakland, CA (US)

(72) Inventors: Piotr Pawel Ruchala, Los Angeles, CA (US); Ewa Dorota Micewicz, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/039,669

(22) PCT Filed: Dec. 19, 2014

(86) PCT No.: PCT/US2014/071531
§ 371 (c)(1),
(2) Date: May 26, 2016

(87) PCT Pub. No.: WO2015/095719
PCT Pub. Date: Jun. 25, 2015

(65) Prior Publication Data
US 2017/0037103 A1    Feb. 9, 2017

Related U.S. Application Data

(60) Provisional application No. 61/919,521, filed on Dec. 20, 2013.

(51) Int. Cl.
| C07K 14/575 | (2006.01) |
| A61K 38/22 | (2006.01) |
| A61K 47/48 | (2006.01) |
| A61K 47/54 | (2017.01) |
| A61K 38/00 | (2006.01) |

(52) U.S. Cl.
CPC ............ *C07K 14/575* (2013.01); *A61K 38/22* (2013.01); *A61K 47/543* (2017.08); *C07K 14/5759* (2013.01); *A61K 38/00* (2013.01)

(58) Field of Classification Search
None
See application file for complete search history.

(56) References Cited

U.S. PATENT DOCUMENTS

| 9,328,140 B2 * | 5/2016 | Ganz .................... C07K 14/575 |
| 2010/0286035 A1 | 11/2010 | Ohtaki et al. |
| 2011/0294735 A1 | 12/2011 | Marsh et al. |
| 2011/0301079 A1 | 12/2011 | Marsh et al. |

FOREIGN PATENT DOCUMENTS

| WO | 2008-021560 A2 | 2/2008 |
| WO | WO-2013086143 A1 * | 6/2013 ........... C07K 14/575 |

OTHER PUBLICATIONS

Neuner et al., 'Development of a neuromedin U-human serum albumin conjugate as a long-acting candidate for the treatment of obesity and diabetes. Comparison with the PEGylated peptide' Journal of Peptide Science, vol. 20, No. 1, pp. 7-19 (E-pub. Nov. 13, 2013).

* cited by examiner

*Primary Examiner* — Robert C Hayes
(74) *Attorney, Agent, or Firm* — Pamela J. Sherwood; Bozicevic, Field & Francis LLP

(57) ABSTRACT

The invention relates to polypeptides referred to herein as NMU analog peptides. NMU analog peptides regulate energy homeostasis.

5 Claims, 8 Drawing Sheets
Specification includes a Sequence Listing.

ANTI-OBESITY COMPOUNDS DERIVED FROM NEUROMEDIN U

INTRODUCTION

Polypeptide hormones and their receptors play important roles in the maintenance of homeostasis in multicellular organisms. Obesity is a leading preventable cause of death worldwide, with increasing prevalence in adults and children, it has became one of the most serious public health problems of the 21st century. Generally, obesity increases the likelihood of various diseases, particularly heart disease, type 2 diabetes, obstructive sleep apnea, certain types of cancer, and osteoarthritis.

Currently, therapeutics capable to reduce appetite and increase energy expenditure are of high interest, and gut peptides which regulate energy homeostasis represent attractive leads. Neuromedin U (NMU) is a highly conserved, endogenous peptide that is implicated in a number of physiological processes including nociception, stress, inflammation, blood pressure, feeding, energy homeostasis, and glycemic control. NMU is widely distributed in the body (peripherally and centrally), and its function is mediated by two G-protein coupled receptors (GPCRs): NMUR1 and NMUR26. NMUR1 is predominantly expressed in the peripheral tissues, particularly the gastrointestinal tract, pancreas, uterus and testes, whereas NMUR2 is mainly expressed in the central nervous system (CNS) with the highest levels in the hypothalamus, hippocampus, spinal cord and paraventricular nucleus. In humans, NMU gene variants have been linked to excess body weight. Peripheral administration of NMU reduces food intake and body weight in rodents and birds, as well as increases locomotor activity and core body temperature in rodents with effects primarily being mediated by NMUR2. Moreover, NMU-overexpression in mice results in a lean phenotype with improved glucose homeostasis and NMU-deficient mice develop obesity characterized by hyperphagia, reduced energy expenditure and hyperglycemia.

Notably, the chronic administration of NMU does not cause tachyphylaxis and does significantly improve glucose tolerance in diet-induced obese (DIO) mice. The unfavorable pharmacokinetic properties of NMU (the half-life of NMU after subcutaneous (sc) injection is less than 5 min) were improved by conjugation with polyethylene glycol (PEG) (Bioorg. Med. Chem 2012, 20, 4751) or human serum albumin (J. Pept. Sci. 2013, November 13. doi: 10.1002/psc.2582) showing in both cases long-lasting, potent anorectic, and glucose-normalizing activity. Full length lipid-conjugated (NMU24) and lipid/PEG40-bi-conjugated (NMU25) analogs (Patent EP 1 999 143 B1, 2011, 1-70) of neuromedin U show limited activity.

SUMMARY OF THE INVENTION

Compositions and method are provided to treat or prevent obesity. The invention pertains to the development of anti-obesity and anti-diabetes treatment(s) by the means of administration of an effective dose of short derivatives of an NMU analog, which analogs selected from those set forth herein as SEQ ID NO:2-30, or in Table 1. These short lipidated analogs of NMU possess high binding affinity to both NMUR1 and NMUR2, which is similar to that of a native peptide. Certain analogs contain α,α-disubstituted amino acid(s) (aminoisobutyric acid, Aib) that can confer increased resistance to enzymatic degradation in circulation.

In one embodiment of the invention, NMU analog polypeptides are provided. Such polypeptide analogs may be formulated in a pharmaceutical composition comprising a pharmaceutically acceptable carrier. Therapeutic applications of the NMU analog include administering the NMU analog to an individual to treat a metabolic disorder afflicting the individual. Such disorders include, but are not limited to, obesity, metabolic syndrome or syndrome X, and type II diabetes. Complications of diabetes such as retinopathy may be positively affected thereby as well. Obesity is a comorbidity of and may well contribute to such disease states as diabetes, hypertension, dyslipidemias, cardiovascular disease, gallstones, osteoarthritis and certain forms of cancers.

Administration of one or more of the NMU analog disclosed herein to effect weight loss in an individual may also be useful in preventing such diseases and as part of therapy for any one of the above-recited conditions, as well as others. In other embodiments, there is provided a method for treating a metabolic disease in an individual comprising administering to the individual one or more of the NMU analog s described above. The metabolic disease may be selected from the group consisting of diabetes, metabolic syndrome, hyperglycemia, and obesity and may be administered via a route peripheral to the brain, such as an oral, mucosal, buccal, sublingual, nasal, rectal, subcutaneous, transdermal, intravenous, intramuscular, or intraperitoneal route. Finally, the NMU analog can be administered to an individual to effect a reduction in food intake by the individual, to effect a reduction in weight gain in the individual, to prevent weight gain in the individual, to effect weight loss in the individual, and/or to prevent weight regain in the individual.

The present disclosure further provides for the use of any one or more of the embodiments and aspects of the NMU analog in the manufacture of a medicament for treatment of a metabolic disorder. Disorders include, but are not limited to, obesity, metabolic syndrome or syndrome X, and type II diabetes. Complications of diabetes such as retinopathy may be positively affected thereby as well. Obesity is a comorbidity of and may well contribute to such disease states as diabetes, hypertension, dyslipidemias, cardiovascular disease, gallstones, osteoarthritis and certain forms of cancers. Thus, the present, disclosure provides a pharmaceutical composition comprising one or more of any of the above NMU analog and a pharmaceutically acceptable carrier.

Other aspects of the invention and their features and advantages will become apparent from the following description and the appended claims.

DETAILED DESCRIPTION OF THE INVENTION AND PREFERRED EMBODIMENTS

Figure 1:
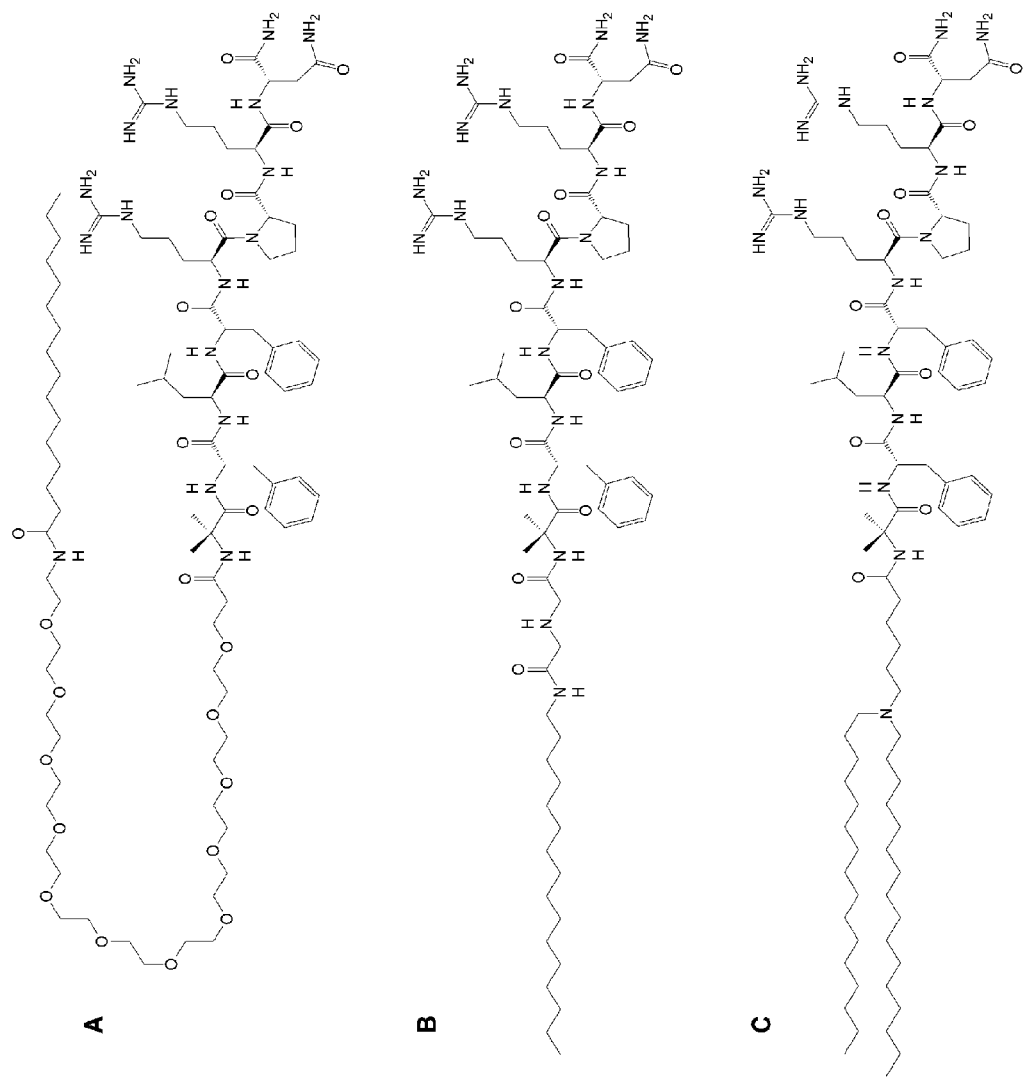
FIG. 1. The most active analogs of neuromedin U synthesized for this study: (A) NM4, (B) NM4A, (C) NM4C$_{16}$.

The peptides of the invention have a number of important physiological functions, including modulation of body weight and metabolism. The NMU analogs of the invention can be efficiently synthesized in large quantities using SPPS technology, giving the final product with a high yield. In addition, the small size of the analog allows for delivery of larger quantities of active ingredient (per mole count) in relatively smaller doses. The use of smaller, lipidated peptide analogs can be advantageous over conjugates with macromolecular carriers due to possible side effects that may be associated with latter.

In some embodiments of the invention, small molecule analogs of human NMU are provided, including without limitation those shown in Table 1. The analogs of the invention include, without limitation, the analogs NM4, NM4A, and NM4$C_{16}$, as shown below (a, b, c, respectively), in which a lipid moiety is conjugated to the peptide FLFRPRN through aminoisobutyric acid (aib). Such analogs have the structure: lipid-aib-FLFRPRN, where the lipid may comprise a $C_{10}$-$C_{20}$ fatty acid or derivative thereof, for example palmitate, N-palmitylamide, dPEG$_{12}$-40-amino-4,7,10,13,16,19,22,25,28,31,34,37-dodecaoxotetradecanoic acid, iminodiacetic acid, (C16)$_2$-6-Aminohexanoic acid, and the like.

In some embodiments the analog has a structure selected from:

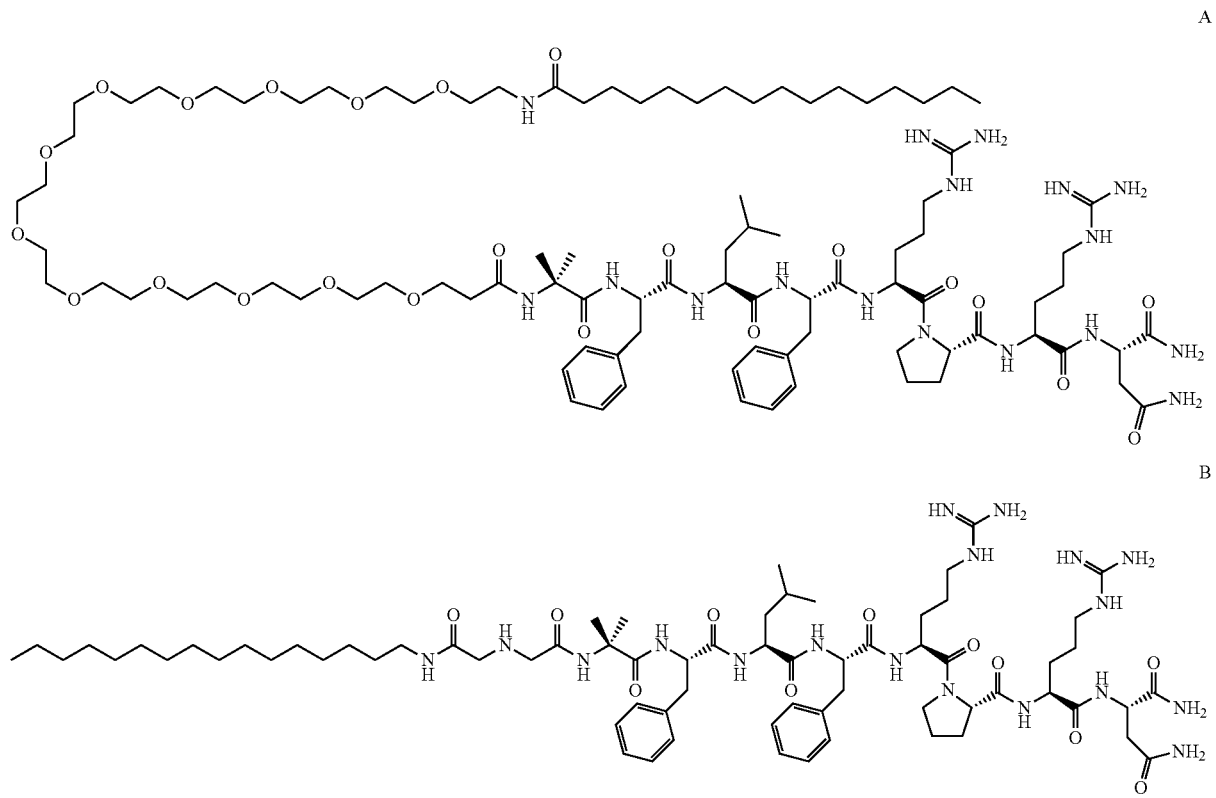

-continued

C

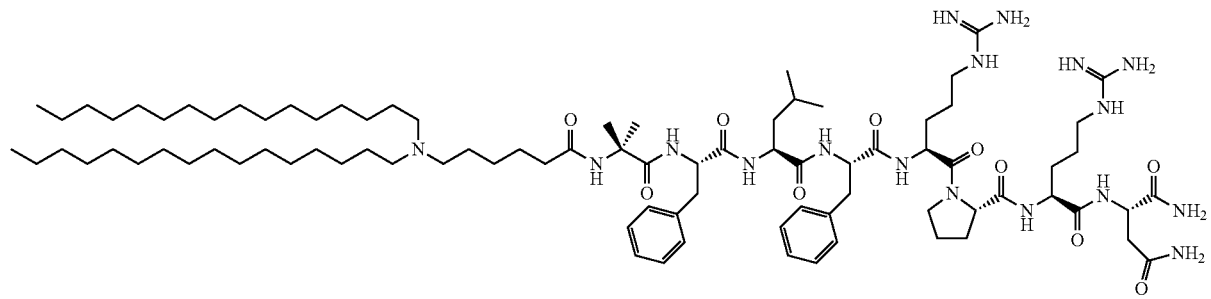

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

NMU analog peptides include those provided herein, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain where the polypeptide is a member of a protein family, or a region associated with a consensus sequence). Variants also include fragments of the polypeptides disclosed herein, for example, biologically active fragments and/or fragments corresponding to functional domains.

Uses of NMU Analog Peptides

In light of the pharmacologic activities of NMU analog peptides, numerous clinical indications are evident. For example, clinical indications for which a NMU analog or variants thereof may find use include treatment of obesity, etc.

Human obesity is a widespread and serious disorder, affecting a high percentage of the adult population in developed countries. In spite of an association with heart disease, type II diabetes, cancer, and other conditions, few persons are able to permanently achieve significant weight loss. The subject peptides are administered to obese patients for purposes of appetite suppression. Patients may use various criteria for determining obesity. Conveniently, a body mass index (BMI) is calculated, where a person having a BMI greater than 25 is overweight and may be considered for treatment with the subject peptides. NMU analog peptides find use in reducing food intake and body weight, as well as increasing locomotor activity and core body temperature, resulting in a lean phenotype with improved glucose homeostasis.

One or more of the NMU analog can be administered to an individual to treat a metabolic disorder afflicting the individual. Such disorders include, but are not limited to, obesity, metabolic syndrome or syndrome X, and type II diabetes. Complications of diabetes such as retinopathy may be positively affected thereby as well. Obesity is a comorbidity of and may well contribute to such disease states as diabetes, hypertension, dyslipidemias, cardiovascular disease, gallstones, osteoarthritis and certain forms of cancers. Administration of one or more of the NMU analog disclosed herein to effect weight loss in an individual may also be useful in preventing such diseases and as part of therapy for any one of the above-recited conditions, as well as others. In other embodiments, there is provided a method for treating a metabolic disease in an individual comprising administering to the individual a one or more of the NMU analog described above. The metabolic disease may be selected from the group consisting of diabetes, metabolic syndrome, hyperglycemia, and obesity and may be administered via a route peripheral to the brain, such as an oral, mucosal, buccal, sublingual, nasal, rectal, subcutaneous, transdermal, intravenous, intra muscular, or intraperitoneal route. In particular embodiments, the NMU analog can be used to treat multiple disorders in an individual. As will be apparent to one of ordinary skill in the art in view of the disclosure herein, the NMU analog can be administered to an individual to effect a reduction in food intake by the individual, to effect a reduction in weight gain in the individual, to prevent weight gain in the individual, to effect weight loss in the individual, and/or to prevent weight regain in the individual In a related embodiment, the treatment of non-insulin-dependent diabetes mellitus (NIDDM) is closely related to the treatment of obesity. NIDDM is a metabolic disease that affects about 5% to 7% of the population in western countries (and 10% of individuals over age 70). It is characterized by hyperglycemia and often accompanied by a number of other conditions, including hypertension, obesity and lipid disturbances. Patients are generally categorized as diabetic or hyperglycemic by measuring the level of glucose in the blood, either directly or by monitoring the level of glycosylated hemoglobin. Treatment is recommended where fasting glucose levels are greater 140 mg/dl, where bedtime glucose is greater than 160 mg/dl, or where $HbA_{1c}$ is greater than 8%. The level of reduction that is desirable depends on the condition of the patient, and the blood glucose levels at the start of treatment, but generally about a 10 to 40% reduction is blood glucose is desirable, usually about a 25 to 35% reduction.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight (continued) previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exorcise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesityrelated disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

Pharmaceutical Compositions

The NMU analogs disclosed herein may be used in a pharmaceutical composition when combined with a pharmaceutically acceptable carrier. Such compositions comprise a therapeutically-effective amount of the NMU analog and a pharmaceutically acceptable carrier. Such a composition may also be comprised of (in addition to NMU analog and a carrier) diluents, fillers, salts, buffers, stabilizers, solubilizers, and other materials well known in the art. Compositions comprising the NMU analog can be administered, if desired, in the form of salts provided the salts are pharmaceutically acceptable. Salts may be prepared using standard procedures known to those skilled in the art of synthetic organic chemistry.

The term "individual" is meant to include humans and companion or domesticated animals such as dogs, cats, horses, and the like. Therefore, the compositions comprising formula I are also useful for treating or preventing obesity and obesity-related disorders in cats and dogs. As such, the term "mammal" includes companion animals such as cats and dogs.

The term "pharmaceutically acceptable salts" refers to salts prepared from pharmaceutically acceptable nontoxic bases or acids including inorganic or organic bases and inorganic or organic acids. Salts derived from inorganic bases include aluminium, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulation. It will be understood that, as used herein, references to the NMU analog of the general formula (I) are meant to also include the pharmaceutically acceptable salts.

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration. The NMU analog may be in multimers (for example, heterodimers or homodimers) or complexes with itself or other peptides. As a result, pharmaceutical compositions may comprise one or more NMU analog in such multimeric or complexed form.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially, or simultaneously.

The pharmacological composition can comprise one or more NMU analog; one or more NMU analog and one or more other agents for treating a metabolic disorder; or the pharmacological composition comprising the one or more NMU analog can be used concurrently with a pharmacological composition comprising an agent for treating a metabolic disorder. Such disorders include, but are not limited to, obesity, metabolic syndrome or syndrome X, type II diabetes, complications of diabetes, hypertension, dyslipidemias, cardiovascular disease, gallstones, osteoarthritis, and certain forms of cancers.

When the pharmacological composition comprises another agent for treating a metabolic disorder, or the treatment includes a second pharmacological composition comprising an agent for treating a metabolic disorder, second agents may include, without limitation, cannabinoid (CB1) receptor antagonists, glucagon like peptide 1 (GLP-1) receptor agonists, lipase inhibitors, leptin, tetrahydrolipstatin, 2-4-dinitrophenol, acarbose, sibutramine, phentamine, fat absorption blockers, simvastatin, mevastatin, ezetimibe, atorvastatin, sitagliptin, metformin, orlistat, Qnexa, topiramate, naltrexone, bupriopion, phentermine, losartan, losartan with hydrochlorothiazide, and the like.

Methods of administrating the pharmacological compositions comprising the one or more NMU analog(s) to an individual include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and-can be administered together with other biologically-active agents. Administration can be systemic or local. In addition, it may be advantageous to administer the composition into the central nervous system by any suitable route, including intraventricular and intrathecal injection. Intraventricular injection may be facilitated by an intraventricular catheter attached to a reservoir (for example, an Ommaya reservoir). Pulmonary administration may also be employed by use of an inhaler or nebulizer, and formulation with an aerosolizing agent. It may also be desirable to administer the one or more NMU analog locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the NMU analog including, but not limited to, encapsulation in liposomes, microparticles, microcapsules; minicells; polymers; capsules; tablets; and the like. In one embodiment, the NMU analog may be delivered in a vesicle, in particular a liposome. In a liposome, the NMU analog is combined, in addition to other pharmaceutically acceptable carriers, with amphipathic agents such as lipids which exist in aggregated form as micelles, insoluble monolayers, liquid crystals, or lamellar layers in aqueous solution.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

An effective dose will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the composition with which to treat each individual patient. Initially, the attending physician will administer low doses of the composition and observe the patient's response. Larger doses of the composition may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. However, suitable dosage ranges for intravenous administration of the compositions comprising the NMU analog may be generally about 5-500 micrograms (Pg) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Ultimately the attending physician will decide on the appropriate duration of therapy using compositions comprising the NMU analog of the present invention. Dosage will also vary according to the age, weight and response of the individual patient.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

Further provided is a pharmaceutical pack or kit, comprising one or more containers filled with one or more of the ingredients of the pharmaceutical compositions and NMU analog. Optionally associated with such container(s) may be a notice in the form prescribed by a governmental agency regulating the manufacture, use or sale of pharmaceuticals or biological products, which notice reflects approval by the agency of manufacture, use or sale for human administration.

EXPERIMENTAL

The following examples are put forth for illustrative purposes, and are not intended to limit the scope of what the inventors regard as their invention. Unless indicated otherwise, parts are parts by weight, molecular weight is weight average molecular weight, temperature is in degrees Celsius, and pressure is at or near atmospheric.

Example 1

To test whether neuromedin U can be modified/derivatized to yield truncated bioactive compound(s) that may be useful as therapeutics, we synthesized a small library (25 peptides) of hNMU analogs utilizing various stabilization protocols, including: cyclization, lipidation, introduction of α,α-disubstituted and N-methylated amino acids, retro-inverso-approach, and combination of such (see Table 1). Subsequently all analogues were tested against human neuromedin U receptors (NMUR1 and NMUR2) in calcium mobilization assay (collaboration with Dr Gary Willars, University of Leicester, UK).

Analytical data for synthesized peptides as well as EC50 values for both receptors are presented in Table 1. Representative calcium mobilization assay dose response experiments are shown in FIG. 1. The most active analog in vitro is NM4 (see FIG. 2). NM4 possesses high binding affinity to both NMUR1 and NMUR2, which is similar to that of a native human neuromedin U, and contains α,α-disubstituted amino acid (aminoisobutyric acid, Aib) that possibly confers increased resistance to enzymatic degradation making NM4 suitable leading

TABLE 1

Sequences, analytical data and in vitro activity data (EC$_{50}$ values) obtained for synthesized hNMU analogs.

| Peptide | Sequence | Composition | MW Calc/ Found | R$_T$ [min] | NMUR1 EC$_{50}$ [nM] | NMUR2 EC$_{50}$ [nM] |
|---|---|---|---|---|---|---|
| hNMU | FRVDEEFQSPFASQSRGY-FL-Phe-Arg-Pro-R-Asn | C$_{141}$H$_{203}$N$_{41}$O$_{38}$ | 3080.41/ 3080.91 | 32.23 | 1.12 ± 0.27 | 0.49 ± 0.13 |
| M1 | Ac-FL-Phe-Arg-Pro-R-Asn | C$_{47}$H$_{71}$N$_{16}$O$_9$ | 990.17/ 990.96 | 30.74 | 0.58 ± 0.14 | 0.60 ± 0.19 |
| M2 | Aib-FL-Phe-Arg-Pro-R-Asn | C$_{49}$H$_{76}$N$_{16}$O$_9$ | 1033.24/ 1034.14 | 25.77 | 0.63 ± 0.25 | 0.21 ± 0.07 |
| M3 | Pal-Aib-FL-Phe-Arg-Pro-R-Asn | C$_{65}$H$_{106}$N$_{16}$O$_{10}$ | 1271.65/ 1272.79 | 64.44 | 331.13 ± 74.09 | 169.82 ± 34.93 |
| M31 | Pal-Aib-FL-Phe-N$^{Me}$R-Pro-R-N$^{Me}$N | C$_{67}$H$_{110}$N$_{16}$O$_{10}$ | 1299.71/ 1300.86 | 57.24* | NA | NA |
| M32 | Pal-Aib-FL-N$^{Me}$F-Arg-Pro-R-N$^{Me}$N | C$_{67}$H$_{110}$N$_{16}$O$_{10}$ | 1299.71/ 1300.98 | 57.16* | NA | NA |
| M33 | Pal-Aib-FL-α$^{Me}$F-Arg-Pro-R-N$^{Me}$N | C$_{67}$H$_{110}$N$_{16}$O$_{10}$ | 1299.71/ 1300.89 | 56.22* | NA | NA |

TABLE 1-continued

Sequences, analytical data and in vitro activity data (EC$_{50}$ values) obtained for synthesized hNMU analogs.

| Peptide | Sequence | Composition | MW Calc/ Found | R$_T$ [min] | NMUR1 EC$_{50}$ [nM] | NMUR2 EC$_{50}$ [nM] |
|---|---|---|---|---|---|---|
| M34 | Pal-Aib-FL-Phe-N$^{Me}$R-Pro-R-N$^{Me}$N | C$_{67}$H$_{110}$N$_{16}$O$_{10}$ | 1299.71/ 1301.14 | 56.41* | NA | NA |
| M35 | Pal-Aib-FL-N$^{Me}$F-Arg-Pro-R-N$^{Me}$N | C$_{67}$H$_{110}$N$_{16}$O$_{10}$ | 1299.71/ 1300.96 | 55.85* | NA | NA |
| M36 | Pal-Aib-FL-α$^{Me}$F-Arg-Pro-R-N$^{Me}$N | C$_{67}$H$_{110}$N$_{16}$O$_{10}$ | 1299.71/ 1301.11 | 55.13* | NA | NA |
| M3D1 | CT-Ida$^{NHPal}$-FL-Phe-Arg-Pro-R-Asn-NT | C$_{65}$H$_{107}$N$_{17}$O$_{10}$ | 1286.67/ 1287.44 | 50.30* | NA | NA |
| M3D2 | CT-Ida$^{NHPal}$-Ahx-FL-Phe-Arg-Pro-R-Asn-NT | C$_{71}$H$_{118}$N$_{6}$O$_{11}$ | 1399.83/ 1400.21 | 49.76* | NA | NA |
| M3D3 | CT-Ida$^{NHPal}$-Ahx-Aib-FL-Phe-Arg-Pro-R-Asn-NT | C$_{75}$H$_{125}$N$_{19}$O$_{12}$ | 1484.93/ 1485.29 | 50.34* | NA | NA |
| M4 | Pal-dPEG$_{12}$-Aib-FL-Phe-Arg-Pro-R-Asn | C$_{92}$H$_{159}$N$_{17}$O$_{23}$ | 1871.37/ 1872.04 | 58.82 | 1.51 ± 0.56 | 1.70 ± 0.29 |
| M4A | Ida$^{NHPal}$-Aib-FL-Phe-Arg-Pro-R-Asn | C$_{69}$H$_{114}$N$_{18}$O$_{11}$ | 1371.77/ 1372.21 | 49.28* | 7.41 ± 0.68 | 6.46 ± 0.89 |
| M4A-C$_{16}$ | C$_{16}$-Ida$^{NHPal}$-Aib-FL-Phe-Arg-Pro-R-Asn | C$_{85}$H$_{146}$N$_{18}$O$_{11}$ | 1596.18/ 1596.36 | 63.19* | NA | NA |
| M4A-Nic | Nic-Ida$^{NHPal}$-Aib-FL-Phe-Arg-Pro-R-Asn | C$_{75}$H$_{117}$N$_{19}$O$_{12}$ | 1476.85/ 1476.89 | 53.64* | 43.65 ± 4.03 | 31.62 ± 1.50 |
| M4-C$_{16}$ | (c$_{16}$)$_2$-Ahx-Aib-FL-Phe-Arg-Pro-R-Asn | C$_{87}$H$_{151}$N$_{17}$O$_{10}$ | 1595.24/ 1595.28 | 63.70* | 549.54 ± 37.99 | 741.30 ± 32.00 |
| M5 | Aib-FL-Phe-Arg-Pro-R-Asn-Aib | C$_{53}$H$_{83}$N$_{17}$O$_{10}$ | 1118.34/ 1118.62 | 26.22 | 58.88 ± 12.11 | 50.12 ± 16.23 |
| M6 | Pal-Aib-FL-Phe-Arg-Pro-R-Asn-Aib | C$_{69}$H$_{113}$N$_{1}$O$_{11}$ | 1356.76/ 1356.82 | 64.48 | NA | NA |
| M7 | Pal-dPEG$_{12}$-Aib-FL-Phe-Arg-Pro-R-Asn-Aib | C$_{96}$H$_{166}$N$_{18}$O$_{24}$ | 1956.48/ 1956.82 | 58.79 | 169.82 ± 41.00 | 100 ± 25.87 |
| M8 | C-Ahx-FL-Phe-Arg-Pro-R-Asn-Ahx-C | C$_{63}$H$_{101}$N$_{19}$O$_{12}$S$_{2}$ | 1380.73/ 1381.99 | 30.65 | 186.21 ± 51.31 | 239.88 ± 35.71 |
| NM9 | C-Ahx-FL-Phe-Arg-Oic-R-Asn-Ahx-C | C$_{67}$H$_{107}$N$_{19}$O$_{12}$S$_{2}$ | 1434.82/ 1435.46 | 33.00 | 1,412.54 ± 237.64 | 707.95 ± 170.91 |
| NM10 | C-Ahx-FL-Phe-Arg-Tic-R-Asn-Ahx-C | C$_{68}$H$_{103}$N$_{19}$O$_{12}$S$_{2}$ | 1442.80/ 1443.57 | 33.69 | 3,981.07 ± 432.94 | 2,691.53 ± 553.57 |
| NM11 | X(C-Ahx-FL-Phe-Arg-Pro-R-Asn-Ahx-C) | C$_{71}$H$_{107}$N$_{19}$O$_{12}$S$_{2}$ | 1482.87/ 1484.28 | 33.69 | NA | NA |
| NM12 | X(C-Ahx-FL-Phe-Arg-Oic-R-Asn-Ahx-C) | C$_{75}$H$_{113}$N$_{19}$O$_{12}$S$_{2}$ | 1536.96/ 1538.37 | 35.33 | NA | NA |
| NM13 | X(C-Ahx-FL-Phe-Arg-Tic-R-Asn-Ahx-C) | C$_{76}$H$_{109}$N$_{19}$O$_{12}$S$_{2}$ | 1544.94/ 1545.62 | 35.93 | NA | NA |
| NM14 | PalS-X(C-Ahx-FL-Phe-Arg-Pro-R-Asn-Ahx-C) | C$_{88}$H$_{141}$N$_{19}$O$_{12}$S$_{3}$ | 1753.38/ 1753.97 | 60.53 | 1,80.38 ± 357.09 | 1,000.00 ± 187.17 |

TABLE 1-continued

Sequences, analytical data and in vitro activity data (EC$_{50}$ values) obtained for synthesized hNMU analogs.

| Peptide | Sequence | Composition | MW Calc/ Found | R$_T$ [min] | NMUR1 EC$_{50}$ [nM] | NMUR2 EC$_{50}$ [nM] |
|---|---|---|---|---|---|---|
| NM15 | PalS-X(C-Ahx-FL-Phe-Arg-Oic-R-Asn-Ahx-C) | C$_{92}$H$_{147}$N$_{19}$O$_{12}$S$_3$ | 1807.47/ 1807.82 | 60.77 | NA | NA |
| NM16 | PalS-X(C-Ahx-FL-Phe-Arg-Tic-R-Asn-Ahx-C) | C$_{93}$H$_{143}$N$_{19}$O$_{12}$S$_3$ | 1815.45/ 1816.37 | 61.51 | 3,981.07 ± 890.78 | NA |

All peptides were synthesized as C-terminal amides, NM3D1 ÷ D3 are all (D)-retro-inverso-analogs where: NT-N-terminus, CT-C-terminus of peptide(s). Abbreviations: Ahx-6-Aminohexanoic acid, Aib-Aminoisobutyric acid, Ida-Iminodiacetic acid, α$^{Me}$F-α-Methyl-L-phenylalanine, N$^{Me}$R-N$^α$-Methyl-L-arginine, N$^{Me}$N-N-Methyl-L-asparagine, N$^{Me}$F-N-Methyl-L-phenylalanine Oic-(2S, 3aS,7aS)-Octahydro-1H-indole-2-carboxylic acid, Tic-(3S)-1,2,3,4-Tetrahydroisoquinoline-3-carboxylic acid, Pal-palmitic acid, PalS-X-3,5-bis(Methyl-S-cysteinyl)-1-(methyl-S-palmityl)-benzene, X-1,3-bis(Methyl-S-cysteinyl)-benzene, NHPal-N-Palmitylamide, dPEG$_{12}$-40-Amino-4,7,10,13,16,19,22,25,28,31,34,37-dodecaoxotetradecanoic acid, NA-not active. Analytical RP-HPLC profiles were obtained with an analytical reversed-phase C18 SymmetryShield™ RP18 column, 4.6 × 250 mm, 5 μm (Waters Corp., Milford, MA) or (*) an analytical reversed-phase XBridge™ BEH300 C4 column, 4.6 × 150 mm, 3.5 μm (Waters Corp., Milford, MA). EC$_{50}$ values were obtained using calcium mobilization assay

| Sequences | |
|---|---|
| hNMU | SEQ ID NO: 1 |
| NM1 | SEQ ID NO: 2 |
| NM2 | SEQ ID NO: 3 |
| NM3 | SEQ ID NO: 4 |
| NM31 | SEQ ID NO: 5 |
| NM32 | SEQ ID NO: 6 |
| NM33 | SEQ ID NO: 7 |
| NM34 | SEQ ID NO: 8 |
| NM35 | SEQ ID NO: 9 |
| NM36 | SEQ ID NO: 10 |
| NM3D1 | SEQ ID NO: 11 |
| NM3D2 | SEQ ID NO: 12 |
| NM3D3 | SEQ ID NO: 13 |
| NM4 | SEQ ID NO: 14 |
| NM4A | SEQ ID NO: 15 |
| NM4A-C$_{16}$ | SEQ ID NO: 16 |
| NM4A-Nic | SEQ ID NO: 17 |
| NM4-C$_{16}$ | SEQ ID NO: 18 |
| NM5 | SEQ ID NO: 19 |
| NM6 | SEQ ID NO: 20 |
| NM7 | SEQ ID NO: 21 |
| NM8 | SEQ ID NO: 22 |
| NM9 | SEQ ID NO: 23 |
| NM10 | SEQ ID NO: 24 |
| NM11 | SEQ ID NO: 25 |
| NM12 | SEQ ID NO: 26 |
| NM13 | SEQ ID NO: 27 |
| NM14 | SEQ ID NO: 28 |
| NM15 | SEQ ID NO: 29 |
| NM16 | SEQ ID NO: 30 |
| FLFRPRN | SEQ ID NO: 31 |

Example 2

Small Lipidated Anti-Obesity Compounds Derived from Neuromedin U

Obesity is a leading preventable cause of death worldwide, with increasing prevalence in adults and children, which became one of the most serious public health problems of the 21$^{st}$ century. Generally, obesity increases the likelihood of various diseases, particularly heart disease, type 2 diabetes, obstructive sleep apnea, certain types of cancer, and osteoarthritis. Currently, therapeutics capable to reduce appetite and increase energy expenditure are of high interest, and gut peptides which regulate energy homeostasis represent attractive leads. Neuromedin U (NMU) is a highly conserved, endogenous peptide that is implicated in a number of physiological processes including nociception, stress, inflammation, blood pressure, feeding, energy homeostasis, and glycemic control. NMU is widely distributed in the body (peripherally and centrally), and its function is mediated by two G-protein coupled receptors (GPCRs): NMUR1 and NMUR2.

NMUR1 is predominantly expressed in the peripheral tissues, particularly the gastrointestinal tract, pancreas, uterus and testes, whereas NMUR2 is mainly expressed in the central nervous system (CNS) with the highest levels in the hypothalamus, hippocampus, spinal cord and paraventricular nucleus. In humans, NMU gene variants have been linked to excess body weight. Peripheral administration of NMU reduces food intake and body weight in rodents and birds, as well as increases locomotor activity and core body temperature in rodents with effects primarily being mediated by NMUR2. Moreover, NMU-overexpression in mice results in a lean phenotype with improved glucose homeostasis and NMU-deficient mice develop obesity characterized by hyperphagia, reduced energy expenditure and hyperglycemia. Notably, the chronic administration of NMU does not cause tachyphylaxis and significantly improve glucose tolerance in diet-induced obese (DIO) mice.

The unfavorable pharmacokinetic properties of NMU (the half-life of NMU after subcutaneous (Sc) injection is less than 5 min) were improved by conjugation with polyethylene glycol (PEG) or human serum albumin (HSA) showing in both cases long-lasting, potent anorectic, and glucose-normalizing activity. Full length lipid-conjugated (NMU24) and lipid/PEG40-bi-conjugated (NMU25) analogs of neuromedin U showed limited activity.

Lipidated and additionally stabilized short peptides derived from hormones were shown to be suitable agents for hormone-replacement therapy. To test whether neuromedin U can be modified/derivatized to yield similar type of compound(s), we synthesized small library (Table 1) of truncated neuromedin U analogs utilizing various stabilization protocols, including: cyclization, lipidation, introduction of α,α-disubstituted amino acids, retro-inverso-approach, and combination of such. All peptides were synthesized as C-terminal amides using standard Fmoc protocol. Generally lipidation was achieved by N-terminal conjugation of palmitic acid. However in the case of retro-inverso derivatives and NM4A we used iminodiacetic acid mono-N-palmityl amide (IdaNHPal, see FIG. 1), which we previously found to be useful lipidation moiety. Double-lipidated analogs, NM4A-C16 and NM4-C16, were synthesized by reductive alkylation using previously described protocol. As starting materials NM4A and Ahx-Aib-FL- FRPRN-amide were employed respectively. Reaction(s) were carried out "in solution" (1,4-dioxane:CH3OH:H2O/ 5:4:1) with excess of 1-hexadecanal (50 eq) and sodium cyanoborohydride (NaBH3CN, 100 eq) as reductive agent. Cyclic analogs NM11-NM16 were synthesized from linear counterparts (NM8-NM10) using published S-alkylation protocol40. Reaction(s) were carried out in 50% solution of DMSO in DMF in the presence of cesium carbonate ($Cs_2CO_3$) and tetrabutylammonium iodide (TBAI), giving all expected analogs with disappointingly low yield (<5%).

Figure 2:
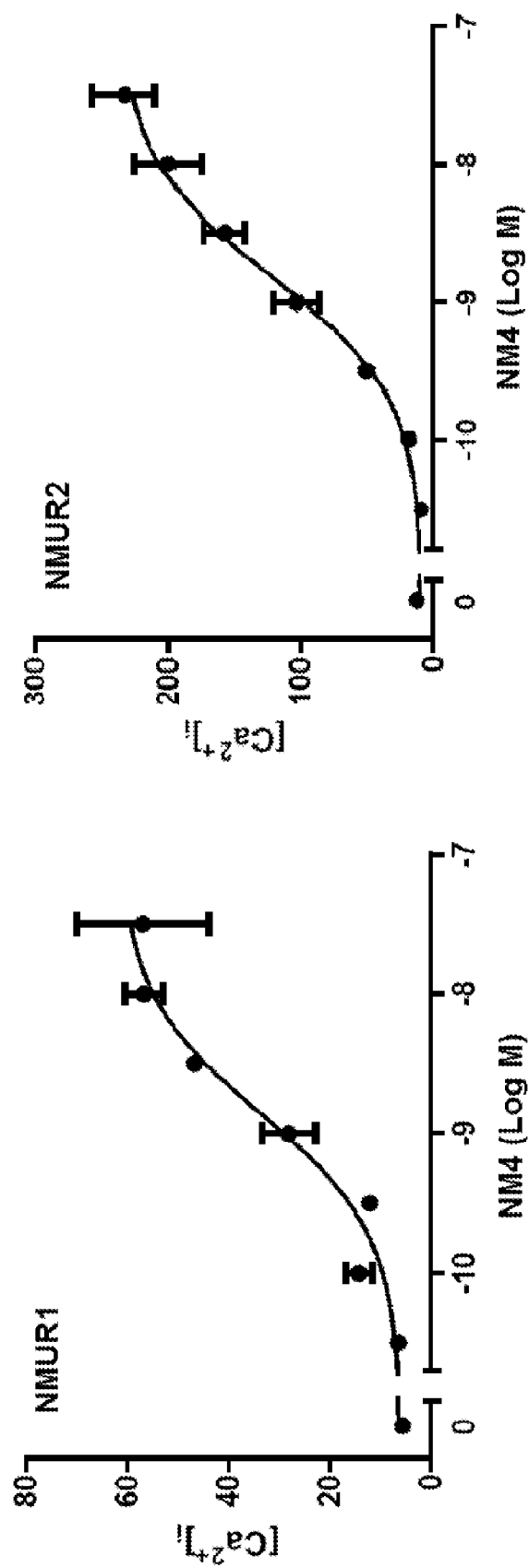
FIG. 2. Calcium mobilization assay: dose response curves obtained for NM4 analog.

All synthesized NM-analogs were tested in vitro using calcium mobilization assay. Examples of dose response curves are shown in FIG. 2. As a result, we found a lipid-conjugated, truncated analog of neuromedin U called NM4 that possesses high binding affinity to both NMUR1 and NMUR2 with affinity similar to that of a native peptide (Table 1, FIG. 1). NM4 contains also α,α-disubstituted amino acid (aminoisobutyric acid, Aib) that may confer increased resistance to enzymatic degradation. Unlike previously described PEG-, and human serum albumin-conjugates that require NMU-carrier conjugation step, NM4 can be efficiently synthesized in large quantities and lipid conjugated using SPPS technology giving final product with a high yield. In addition, NM4 is only 9 amino acids long, which is approximately ⅓ of native human NMU. Taking into account molecular weight of reported conjugates, NM4 is approximately 40 times smaller allowing for delivery of larger quantities of active ingredient (per mole count) in relatively smaller doses. Moreover, use of smaller, palmitoylated peptide(s) can be advantageous over conjugates with macromolecular carriers due to possible side effects that may be associated with latter. Namely, conjugates with human serum albumin may lead to generation of antibody-based immunoresponse and in certain cases hypersensitivity to macromolecular-PEGs was also reported.

Figure 3:
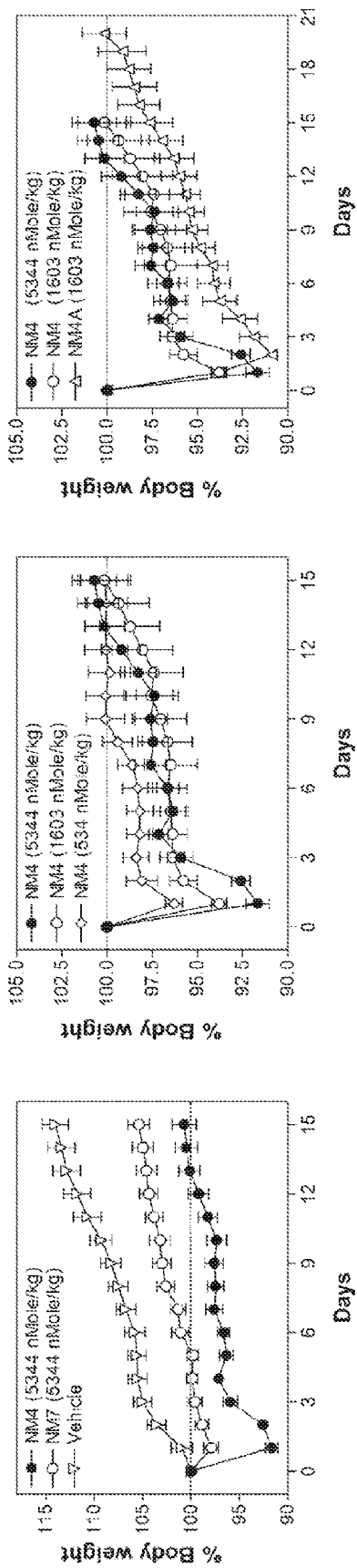
FIG. 3. Single dose in vivo experiments performed in DIO mouse model. (A) Comparison of anorectic effects of NM4 and NM7. (B) NM4 dose response experiments. (C) Comparison of NM4 and NM4A anorectic activity.

To test whether newly synthesized NM analogs possess any in vivo anorectic activity, we compared NM4 and NM7 peptides in diet induced obese (DIO) mouse model using previously described protocols. Initially we focused on single dose experiments comparing NM4 and NM7 at 5344 nMole/kg dose (FIG. 3). NM7 was used as an alternative lead compound because it contains two Aib residues that should confer even greater resistance to the degradation in circulation, which may compensate for lower binding affinity and produce equal to NM4 or better biological effects. Since palmitoylated analogues have limited water solubility we employed phospholipid-based, commercially available drug delivery system, PUREBRIGHT® SL-220 (NOF America Corp., White Plains, N.Y.) that is suitable for delivery of lipidated peptides.

Direct comparison revealed that in single dose experiment(s) NM4 shows significant anorectic activity (FIG. 3A) and observed effects are dose-dependent (FIG. 3B). However NM4 contains in its structure $dPEG_{12}$ linker (40-amino-4,7,10,13,16,19,22,25,28,31,34,37-dodecaoxotetradecanoic acid, Peptides International, Inc., Louisville, Ky.)) which is particularly expensive and significantly contribute to final price of peptide production. Therefore we sought less expensive alternative(s) which resulted in the discovery of "PEG-free" NM4A analog (FIG. 1) which utilized N-terminal iminodiacetic acid mono-N-palmityl amide ($Ida^{NHPal}$). Obtained analog possesses similar bioactivity and is ~10 times less expensive to produce then parental NM4. Subsequent in vivo testing revealed that NM4A is at least 3.5 times more active than NM4 and its anorectic effects after single dose administration (1603 nMole/kg; 2.2 mg/kg) may last up to ~20 days (FIG. 3C).

Figure 4:
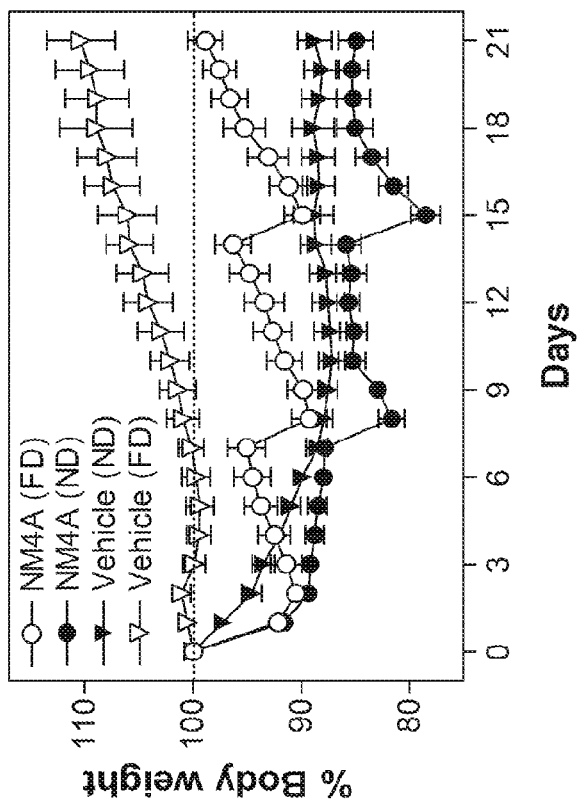
FIG. 4. Anorectic effects of NM4A in chronic in vivo experiments. (A) Ad libitum fed male DIO C57BL/6 mice were treated with either vehicle or NM4A (2.2 mg/kg; 1603 nMole/kg) every 2, 4 or 7 days for 21 days. (B) Ad libitum fed male DIO C57BL/6 mice were treated with either vehicle or NM4A (2.2 mg/kg; 1603 nMole/kg) once a week for 21 days. After initial treatment animals were kept either on high-fat diet (FD) or normal diet (ND).
Figure 4:
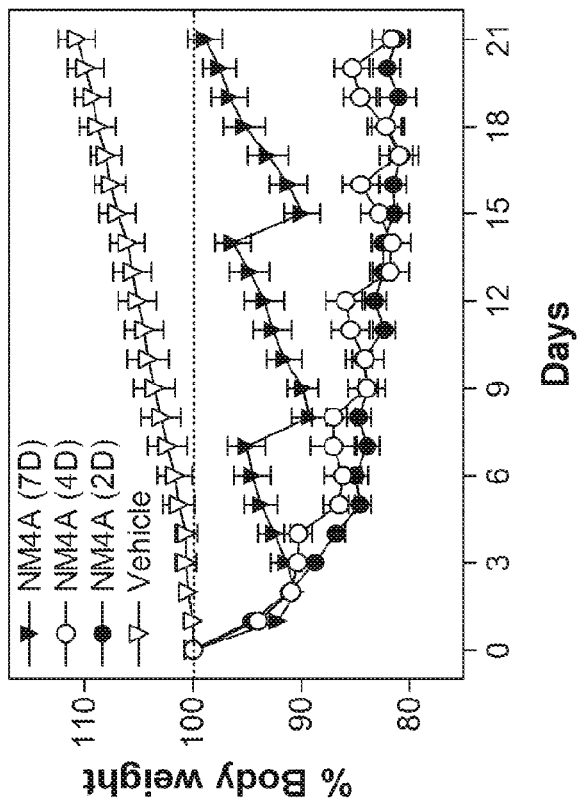

NM4A was characterized further in in vivo chronic experiments. Ad libitum fed male DIO C57BL/6 mice, which were kept on the high fat diet (Cat #D12492, Research Diets, Inc., New Brunswick, N.J.), were treated subcutaneously (s.c.) with either vehicle or NM4A (2.2 mg/kg; 1603 nMole/kg) either every 2, 4 or 7 days for 21 days. As shown on FIG. 4A, NM4A exerts potent anorectic effects at every 2 and every 4 days injections regimens with less frequent dosage showing limited activity in the chronic settings. Notably s.c. administration of the NM4A at above mentioned doses causes initially gastric emptying in experimental animals within 24 hours post administration and such effects subsidies in time. To determine whether NM4A can be used as an auxiliary in dieting of the obese subjects we tested its efficiency in once weekly regimen at the 2.2 mg/kg dose. In this case, ad libitum fed male DIO C57BL/6 mice were kept either on the high fat diet (FD) or regular diet (ND) during NM4A's administration. Obtained data suggests that NM4A is beneficial in this case, giving additional body weight decrease (FIG. 4B).

Considering current trends in obesity/diabetes treatment, development of long acting analogs of NMU is highly desirable. Such analogs could be used in combination therapy with incretin-based therapeutic(s) like semaglutide, a long-acting glucagon-like peptide 1 (GLP-1) analog that possesses 160 h plasma half-life. Since NM4A has shown limited activity in once weekly regimen we decided to synthesize additional double-lipidated analogs that theoretically should have improved pharmacokinetic properties, e.g. plasma half-life resulting from increased possibility/strength of hydrophobic interactions with abundant plasma proteins (albumin, HDL, etc.).

Figure 7:
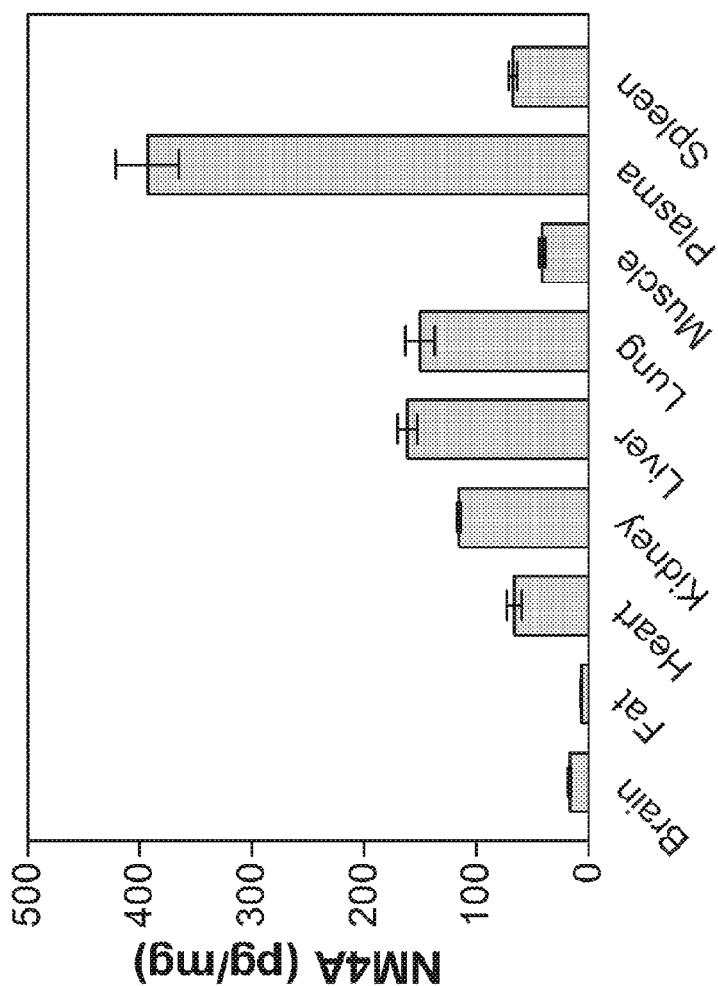
FIG. 7. (A) Abdominal fat evaluation of chronically treated animals. Ad libitum fed male DIO C57BL/6 mice were treated with either vehicle or NM4A (2.2 mg/kg; 1603 nMole/kg) every 2 days or NM4A (2.2 mg/kg; 1603 nMole/kg) every 4 days or (*)NM4-$C_{16}$ (2.6 mg/kg; 1603 nMole/kg) every 7 days for 21 days. Subsequently, their abdominal fat was harvested and weighted. Results are expressed as % of abdominal fat per total body weight. (B) Distribution of NM4A in NM4A chronically treated animals (2.2 mg/kg; every 2 days for 28 days). Subsequently their organs were harvested and analyzed using MDS Sciex QSTAR XL Hybrid Quadrupole Time-of-Flight LC/MS (Applied Biosystems) with methylated NM4A (NM4A-Me) as internal standard.
Figure 7:
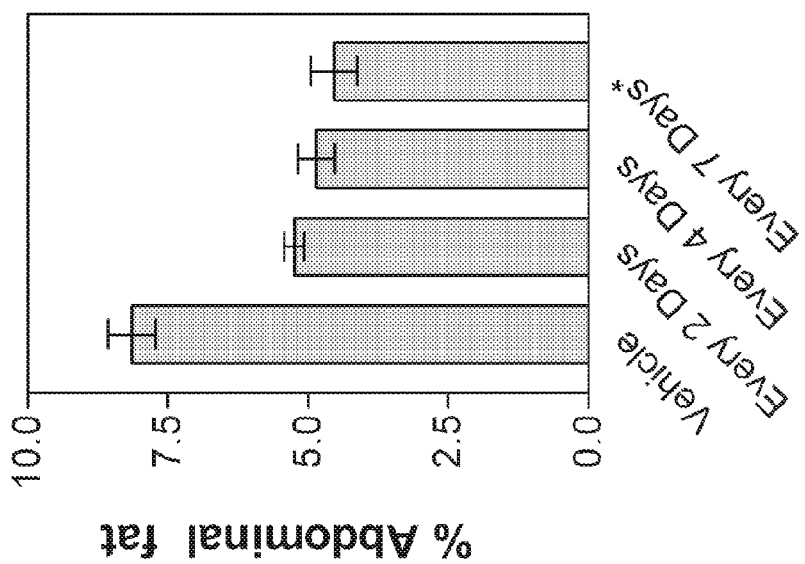

In addition lipid-conjugation may also improve bioactivity by increasing local concentration of the analog(s) in hydrophobic environment of lipid rafts which are enriched in various G protein-coupled receptors (G PCR). Therefore, using reductive-alkylation approach, we synthesized two analogs: NM4A-$C_{16}$ & NM4-$C_{16}$, with varying lipidation points/geometry (FIG. 7). Their in vitro testing revealed that only NM4-$C_{16}$ analog with symmetrical lipidation motif, which is removed from main body of the NM-peptide, possesses potent bioactivity.

Figure 5:
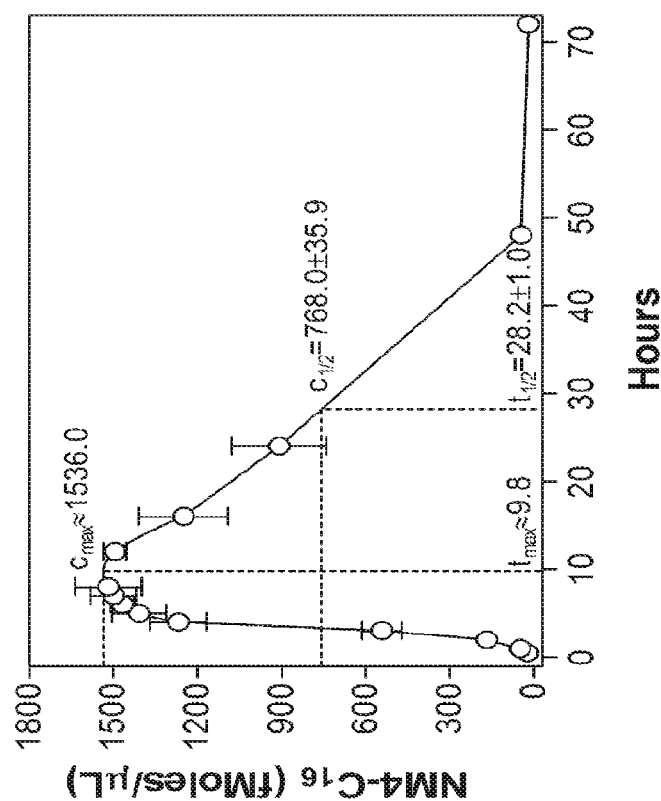
FIG. 5. Pharmacokinetics of NM4A & NM4-$C_{16}$ analogs. Animals were individually dosed with 10 mg/kg of (A) NM4A or (B) NM4-$C_{16}$ and plasma samples collected in indicated time points. LC/MS/MS analysis was performed using MDS Sciex QSTAR XL Hybrid Quadrupole Time-of-Flight LC/MS (Applied Biosystems, Inc., Foster City, Calif.) and methylated NM4A (NM4A-Me) as internal standard.
Figure 5:
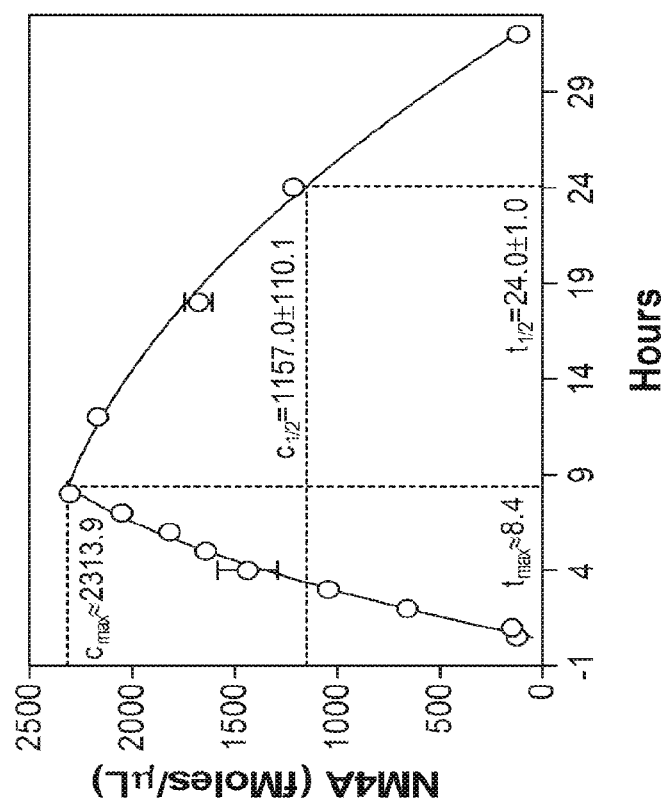

To determine whether our approach yielded analog which may be used in once weekly regiment we performed limited pharmacokinetics studies of NM4A and NM4-$C_{16}$ compounds. Direct comparison revealed that NM4-$C_{16}$ indeed has extended plasma half-life ($t_{1/2}$=28.2±1 h), however in this case effects of double-lipidation are limited (FIG. 5). These results as well as relatively short plasma half-life observed for both PEG- and HSA-NMU conjugates ($t_{1/2}$≈11-54 h, depending on species) may indicate that key factor in this case is rather enzymatic resistance of tested analogs than their ability to persist in the plasma. Further modifications of NM4-$C_{16}$ are also limited due to high specificity of neuromedin receptors. Indeed, our attempts to increase proteolytic resistance of truncated NMU analogs proved largely unsuccessful, with various retro-inverso-, α-carbon-methylated, N-methylated and cyclic analogs being in most cases virtually inactive (Table 1). Nonetheless, data obtained for analogs NM8-16 suggest that substitution of Pro for more rigid and bulky residues, e.g. Oic or Tic, has undesirable effect ($EC_{50}$: NM8<NM9<NM10). Moreover, data comparison between analogs NM8-10 (linear peptides), NM11-13 (cyclic peptides) and NM14-16 (cyclic/lipidated peptides) also suggest that cyclization is not viable option as it renders analogs NM11-13 inactive.

Interestingly, introduction of lipid moiety to the cyclic analogs (NMN14-16) seems, at least partially, to restore bioactivity. These results are generally in line with recently published observations that underline importance of Asn and Pro residues for NMU-receptors' binding. For example modification of Pro in compound 1b leads always to analogs with decreased activity regardless on substituent (e.g. Hyp, compound S4a; L-pipecolic acid, compound S4b; and 1-aminocyclopropane-1-carboxylic acid, compound S4c) with even more profound activity loss observed for modifications of C-terminal Asn residue (compounds S1a-S1e).

Considering additionally inactivity of our retro-inverso-analogs (NM3D1-3) and α-carbon-/N-methylated-variants (NM31-NM35) as well as limited activity of cyclic (NM14) and β-homo-amino acids containing NMU derivatives, further derivatization and/or modifications of NMU for pharmaceutical purposes appears to be difficult. However, the viable modification seem to be introduction of small α,α-disubstituted amino acid(s) (Aib) at the flanking positions of native active sequence (e.g. FLFRPRN). Notably bis-substituted analogs (e.g. X-Aib-FLFRPRN-Aib) show significantly decreased potency in in vitro assays ($EC_{50}$: NM1<NM2<NM5) and very limited activity in vivo (NM7, FIG. 3A). Lipidation itself does not appear to have detrimental effects, provided its position is significantly removed from active portion of the analog(s) ($EC_{50}$: NM4<NM4A<NM7<NM3<NM4A-$C_{16}$).

Figure 6:
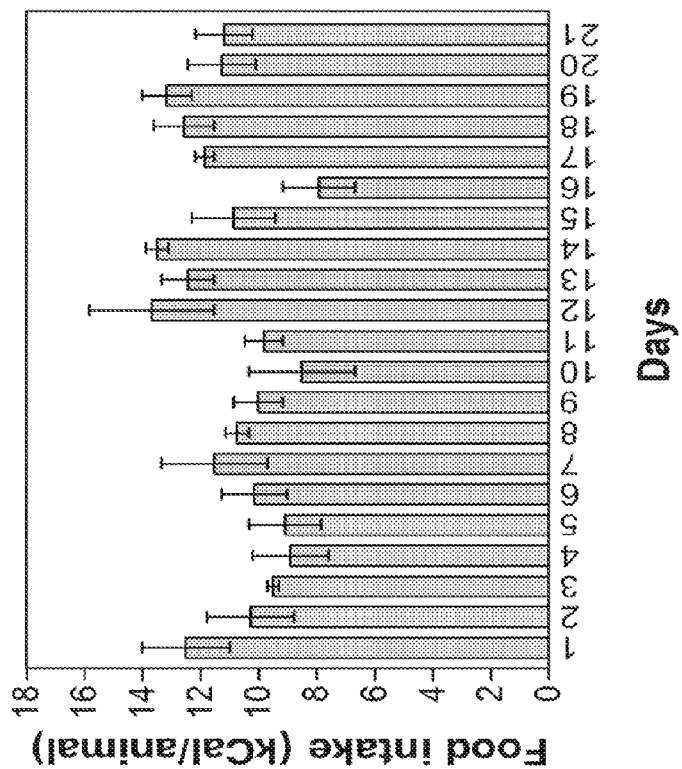
FIG. 6. (A) Comparison of anorectic effects of NM4A & NM4-$C_{16}$ analogs in chronic in vivo experiments. Ad libitum fed male DIO C57BL/6 mice were treated with either vehicle or NM4A (2.2 mg/kg; 1603 nMole/kg) or NM4-$C_{16}$ (2.6 mg/kg; 1603 nMole/kg) every 7 days for 21 days. (B) Food intake of animals treated with NM4-$C_{16}$ (2.6 mg/kg; 1603 nMole/kg) every 7 days for 21 days.
Figure 6:
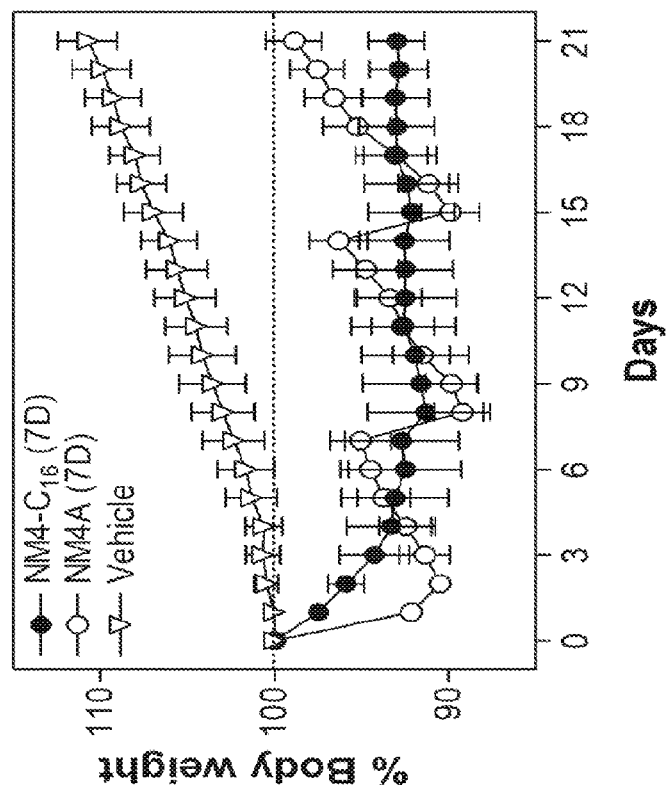

Despite limited success with our "double-lipidation" approach, we decided to test NM4-$C_{16}$ analog in vivo using once weekly subcutaneous injection regimen at the 2.6 mg/kg dose, which is equimolar to previously used NM4A dose (e.g. 1603 nMole/kg). As shown in FIG. 6, once-weekly administration of NM4-$C_{16}$ results in sustained weight loss in DIO mouse model. Moreover, in this case we observed very limited gastric emptying in experimental animals and their hematological parameters/blood cell count appears to be normal (Table 2).

For three groups of animals treated every 2, 4 and 7 days we also performed abdominal fat evaluation (FIG. 7A). Obtained results suggest that chronic treatment with either NM4A or NM4-$C_{16}$ decreases abdominal fat content (~5% versus ~8% for vehicle treatment).

To test body distribution of NM-analogs we performed also limited ADME studies in animals that underwent chronic treatment with NM4A every 2 days for 28 days (2.2 mg/kg; 1603 nMole/kg dose). As shown in FIG. 7B, highest content of NM4A is detected in plasma of experimental animals with significant amounts accumulating also in the liver, lungs and kidneys. Notably NM4A does not appear to enter the brain effectively, suggesting that its biological effects are transduced via NMU receptors present in periphery.

Figure 8:
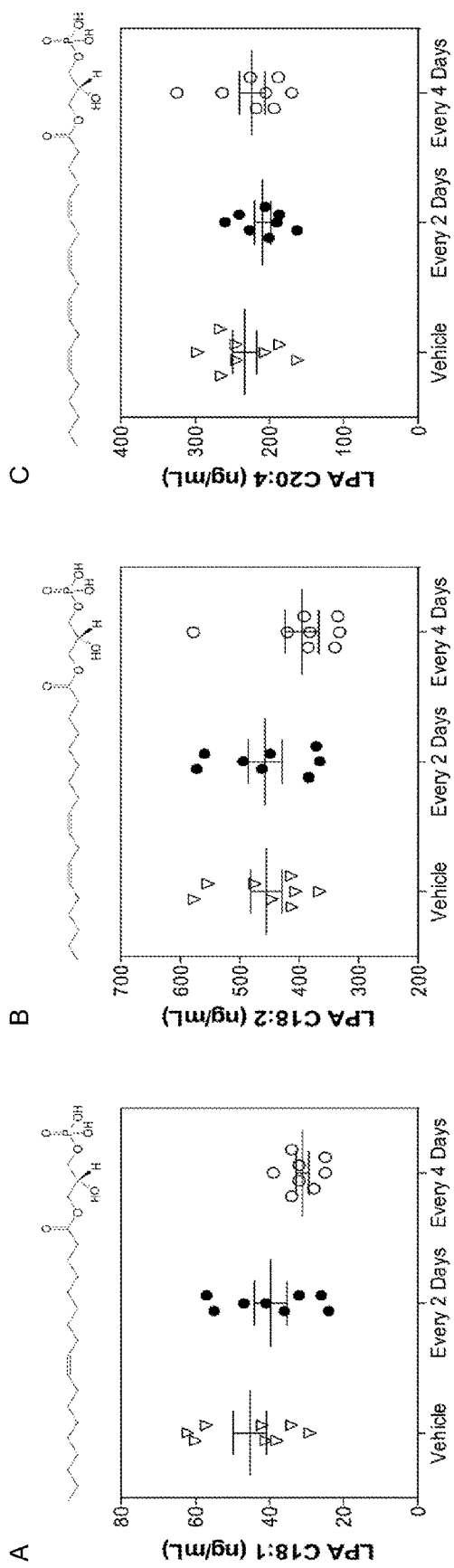
FIG. 8. LPA levels in the plasma of NM4A treated DIO mice (2.2 mg/kg; every 2 or 4 days for 21 days): (A) (18:1)-1-oleoyl-2-hydroxy-sn-glycero-3-phosphatidic acid, (B) (18:2)-1-linoleoyl-2-hydroxy-sn-glycero-3-phosphatidic acid, (C) (20:4)-1-arachidonoyl-2-hydroxy-sn-glycero-3-phosphatidic acid.

To examine whether lipidation and its position has an impact on the secondary structure of synthesized neuromedin analogs, we performed FTIR studies of selected compounds (FIGS. 8 & 9).

TABLE 2

Hematological parameters of animals treated with NM4-$C_{16}$. Ad libitum fed male DIO C57BL/6 mice (high-fat diet) were treated with NM4-$C_{16}$ (2.6 mg/kg; 1603 nMole/kg) every 7 days for 21 days. Blood was collected by cardiac puncture and cells' count evaluated using HemaVet 950FS Hematology Analyzer (Drew Scientific Inc., Dallas, TX)

| Cells | Count/mL |
| --- | --- |
| White Blood Cells | $5.73 \pm 0.49 \times 10^6$ |
| Neutrophils | $1.02 \pm 0.06 \times 10^6$ |
| Lymphocytes | $4.56 \pm 0.43 \times 10^6$ |
| Monocytes | $1.46 \pm 0.14 \times 10^5$ |
| Red Blood Cells | $9.49 \pm 0.31 \times 10^9$ |
| Platelets | $6.95 \pm 0.23 \times 10^8$ |

All peptides were synthesized as C-terminal cysteamine-amides by the solid phase method using CEM Liberty automatic microwave peptide synthesizer (CEM Corporation Inc., Matthews, N.C.), applying 9-fluorenylmethyloxycarbonyl (Fmoc) chemistry and commercially available amino acid derivatives and reagents (EMD Biosciences, San Diego, Calif. and Chem-Impex International, Inc., Wood Dale, Ill.). Cysteamine 2-Chlorotrityl Resin (EMD Biosciences, San Diego, Calif.) was used as a solid support. Peptides were cleaved from resin using modified reagent K (TFA 94% (v/v); phenol, 2% (w/v); water, 2% (v/v); TIS, 1% (v/v); EDT, 1% (v/v); 2 hours) and precipitated by addition of ice-cold diethyl ether. Subsequently, peptides were purified by preparative reverse-phase high performance liquid chromatography (RP-HPLC) and their purity evaluated by matrix-assisted laser desorption ionization spectrometry (MALDI-MS) as well as analytical RP-HPLC.

The analogs NM4A-$C_{16}$, NM4-$C_{16}$ and NM4A-Me (for FTIR and PK studies only) were synthesized from NM4A, Ahx-Aib-FLFRPRN-amide and NM4A respectively. Peptides were dissolved in mixture of 1,4-dioxane, methanol and water (5:4:1) and mixed with proper carbonyl compound (50 eq, 30 min). For analogs NM4A-$C_{16}$ and NM4-$C_{16}$ commercially available 1-hexadecanal was used (Cayman Chemical Company, Ann Arbor, Mich.), and in case of NM4A-Me formalin was employed. Subsequently, acetic acid was added (100 eq) and reaction mixture was placed in ice-bath and mixed for additional 20 min (magnetic stirrer). Subsequently freshly prepared water solution of $NaBH_3CN$ (100 eq) was added dropwise with vigorous mixing and afterwards reaction mixture was agitated for additional 3 hours. Then reaction mixture was further acidified with acetic acid (500 eq), diluted with water (1:1) and freeze-dried. Obtained solid residue(s) were purified by preparative reverse-phase high performance liquid chromatography (RP-HPLC) and their purity evaluated by matrix-assisted laser desorption ionization spectrometry (MALDI-MS) as well as analytical RP-HPLC.

Cyclization of linear analogs NM8-NM10 was performed in 50% solution of DMSO in DMF using 1,3-bis(bromomethyl)benzene (NM11-NM13) or 1-(palmityl-S-methyl)-3,5-bis(bromomethyl)-benzene. Briefly, peptides (2 eq.) were dissolved at final concentration 5 mg/ml. Subsequently anhydrous cesium carbonate ($Cs_2CO_3$, 20 eq.), tetrabutylammonium iodide, (TBAI, 4 eq.) and proper bis(bromomethyl)-benzene-derivative (1 eq) were added. Solution was vigorously mixed on magnetic stirrer and progress of reaction monitored by analytical RP-HPLC. Subsequently peptides were purified and characterized as described in the peptide synthesis section.

HEK293 cells expressing either the neuromedin U 1 receptor or neuromedin U 2 receptor (HEK-NMU1 and HEK-NMU2 respectively) were grown to approximately 90% confluence in ELISA strip plates (96-well format)

pre-coated with poly-D-lysine (0.1% w/v) and loaded for 45 min at 37° C. with 2 iM fluo-4-AM in Krebs'-HEPES buffer with bovine serum albumin (KHB-BSA; composition: 10 mM HEPES; 4.2 mM NaHCO$_3$; 11.7 mM D-glucose; 1.18 mM MgSO$_4$.7H$_2$O; 1.18 mM KH$_2$PO$_4$; 4.69 mM KCl; 118 mM NaCl; 1.3 mM CaCl$_2$.2H$_2$O; 0.1% (w/v) BSA; pH 7.4). Monolayers were then washed and equilibrated for 5 min at 37° C. in 100 il KHB-BSA for subsequent recording of fluorescence as an index of intracellular [Ca$^{2+}$] ([Ca$^{2+}$]$_i$) using a microplate reader (NOVOstar; BMG LABTECH, Aylesbury, U.K.). Briefly, 20 μl of KHB-BSA, with or without ligand, was added into the well (200 μl/s) and fluorescence determined at 0.5 s intervals by excitation at 485 nm and collection of emitted light at 520 nm. Changes in fluorescence above basal levels (before ligand addition) were determined. When required, [Ca$^{2+}$]$_i$ was calculated using the formula: [Ca$^{2+}$]$_i$=K$_d$(F−F$_m$)/(F$_{max}$−F), with the K$_d$ of fluo-4 taken as 350 nM. F$_{max}$ was obtained by removal of buffer and addition of KHB-BSA buffer containing 4 mM [Ca$^{2+}$] and ionomycin (2 μM) to representative wells and the fluorescence measured for 10 min. F$_{min}$ was then derived by replacing buffer with Ca$^{2+}$-free KHB-BSA buffer containing 2 mM EGTA and fluorescence measured for 10 min. For the determination of concentration-response relationships, the maximal change in [Ca$^{2+}$]$_i$ was calculated following ligand addition. Concentration-response curves were then fitted using a four-parameter logistic equation to determine EC$_{50}$ values (GraphPad Software Inc., Calif.).

All animal experiments were approved by the UCLA Animal Care and Use Committee (ARC #1999-173-23) and conformed to local and national guidelines. Ad libitum fed male DIO C57BL/6 mice (n=8 per group) kept on D12492, a high-fat diet composed of 60% Kcal from fat (Research Diets, Inc., New Brunswick, N.J.) were weighed and individually dosed (s.c., 30 min prior to the onset of the dark phase of the light cycle) with either vehicle or NM4A (2.2 mg/kg; 1603 nMole/kg) every 2 days or NM4A (2.2 mg/kg; 1603 nMole/kg) every 4 days or NM4A (2.2 mg/kg; 1603 nMole/kg) every 7 days or NM4-C$_{16}$ (2.6 mg/kg; 1603 nMole/kg) every 7 days for 21 days and their food intake and body weight were measured daily. Due to limited water solubility, lipidated analogs NM4A and NM4-C$_{16}$ were formulated in phospholipid-based, commercially available drug delivery system, PUREBRIGHT® SL-220 (NOF America Corp., White Plains, N.Y.). Briefly, calculated amount of the desired peptide (1 eq) and 10 equivalents of PUREBRIGHT® SL-220 (1 mg: 10 mg) were solubilized in minimal volume of 90% absolute ethyl alcohol in water. Subsequently solution was aliquoted into Eppendorf tubes and freeze-dried. Obtained solid residue was re-solubilized in the proper amount of PBS directly before use by vortexing.

C57BL/6 mice were weighted and individually dosed with either NM4A or NM4-C$_{16}$ at 10 mg/kg dose. Subsequently small samples of blood were collected at indicated time-points and centrifuged (3000 rpm/10 min). Obtained plasma samples were transferred to the 0.5 mL centrifuge tubes and immediately diluted with 4 volumes of DMSO/ACN mixture (1:1) containing 0.1% of TFA. Subsequently samples were centrifuged at 13000 rpm for 10 min and obtained supernatants analyzed using MDS Sciex QSTAR XL Hybrid Quadrupole Time-of-Flight LC/MS (Applied Biosystems, Inc., Foster City, Calif.) with methylated NM4A (NM4A-Me) as internal standard.

Ad libitum fed male DIO C57BL/6 mice that underwent chronic treatment with NM4A (2.2 mg/kg; 1603 nMole/kg; dosing every 2 days for 28 days) were sacrificed and their organs/tissues harvested and weighted. Subsequently 4 volumes of DMSO/ACN mixture (1:1) containing 0.1% of TFA, were added and samples homogenized using rod homogenizer (max. speed for 30 s). Obtained homogenate(s) were transferred to 1.5 mL Eppendorf tubes and centrifuged for 10 min at 13000 rpm. Obtained supernatant(s) were analyzed using MDS Sciex QSTAR XL Hybrid Quadrupole Time-of-Flight LC/MS (Applied Biosystems, Inc., Foster City, Calif.) with methylated NM4A (NM4A-Me) as internal standard.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. Accordingly, it should be understood that the scope of the invention is not limited by this detailed description, but by the appended claims as properly construed under principles of patent law.

What is claimed is:

1. An isolated biologically active peg-free NM4 analog peptide, wherein the peptide consists of a sequence set forth in one of SEQ ID NO: 15 or 18.

2. The peptide of claim 1, formulated with a pharmaceutically acceptable excipient.

3. An isolated biologically active NM4 analog peptide, wherein the peptide comprises of a sequence set forth in one of SEQ ID NO:14, 15 and 18.

4. An isolated biologically active peg-free NM4 analog polypeptide, consisting of the peptide sequence FLFRPRN (SEQ ID NO:31) conjugated to a $C_{10}$-$C_{20}$ fatty acid or derivative thereof through aminoisobutyric acid (Aib) wherein the fatty acid or derivative thereof is selected from palmitate, N-palmitylamide, or $(C_{16})_2$-6-aminohexanoic acid (N,N-di(1-hexadecyl)-6-aminohexanoic acid).

5. A method of regulating one or more of obesity, energy homeostasis, and food intake in an individual, the method comprising:
administering to the individual an effective dose of a peptide according to claim 1.

* * * * *

SEQUENCE LISTING

<160> NUMBER OF SEQ ID NOS: 31

<210> SEQ ID NO 1
<211> LENGTH: 25
<212> TYPE: PRT
<213> ORGANISM: Homo sapiens

<400> SEQUENCE: 1

Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25

<210> SEQ ID NO 2
<211> LENGTH: 7

```
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION

<400> SEQUENCE: 2

Phe Leu Phe Arg Pro Arg Asn
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is aminoisobutyric acid (Aib)

<400> SEQUENCE: 3

Xaa Phe Leu Phe Arg Pro Arg Asn
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)

<400> SEQUENCE: 4

Xaa Phe Leu Phe Arg Pro Arg Asn
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (5)..(5)
<223> OTHER INFORMATION: Xaa is N(alpha)-Methyl-L-arginine
<220> FEATURE:
<221> NAME/KEY: MISC_FEATURE
<222> LOCATION: (8)..(8)
<223> OTHER INFORMATION: Xaa is N-Methyl-L-asparagine

<400> SEQUENCE: 5

Xaa Phe Leu Phe Xaa Pro Arg Xaa
```

-continued

```
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (4)..(4)
<223> OTHER INFORMATION: Xaa is N-Methyl-L-phenylalanine
<220> FEATURE:
<221> NAME/KEY: MISC_FEATURE
<222> LOCATION: (8)..(8)
<223> OTHER INFORMATION: Xaa is N-Methyl-L-asparagine

<400> SEQUENCE: 6

Xaa Phe Leu Xaa Arg Pro Arg Xaa
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (4)..(4)
<223> OTHER INFORMATION: Xaa is (Alpha)-Methyl-L-phenylalanine
<220> FEATURE:
<221> NAME/KEY: MISC_FEATURE
<222> LOCATION: (8)..(8)
<223> OTHER INFORMATION: Xaa is N-Methyl-L-asparagine

<400> SEQUENCE: 7

Xaa Phe Leu Xaa Arg Pro Arg Xaa
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (5)..(5)
<223> OTHER INFORMATION: Xaa is N(alpha)-Methyl-L-arginine
```

<220> FEATURE:
<221> NAME/KEY: MISC_FEATURE
<222> LOCATION: (8)..(8)
<223> OTHER INFORMATION: Xaa is N-Methyl-L-asparagine

<400> SEQUENCE: 8

Xaa Phe Leu Phe Xaa Pro Arg Xaa
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (4)..(4)
<223> OTHER INFORMATION: Xaa is (alpha)-Methyl-L-phenylalanine
<220> FEATURE:
<221> NAME/KEY: MISC_FEATURE
<222> LOCATION: (8)..(8)
<223> OTHER INFORMATION: Xaa is N-Methyl-L-asparagine

<400> SEQUENCE: 9

Xaa Phe Leu Xaa Arg Pro Arg Xaa
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (4)..(4)
<223> OTHER INFORMATION: Xaa is (alpha)-Methyl-L-phenylalanine
<220> FEATURE:
<221> NAME/KEY: MISC_FEATURE
<222> LOCATION: (8)..(8)
<223> OTHER INFORMATION: Xaa is N-Methyl-L-asparagine

<400> SEQUENCE: 10

Xaa Phe Leu Xaa Arg Pro Arg Xaa
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (8)..(8)
<223> OTHER INFORMATION: Xaa is N-terminal iminodiacetic acid mono-N-

-continued palmityl amide

<400> SEQUENCE: 11

Asn Arg Pro Arg Phe Leu Phe Xaa
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (8)..(8)
<223> OTHER INFORMATION: Xaa is 6-Aminohexanoic acid (Ahx)
<220> FEATURE:
<221> NAME/KEY: MISC_FEATURE
<222> LOCATION: (9)..(9)
<223> OTHER INFORMATION: Xaa is N-terminal iminodiacetic acid mono-N-
    palmityl amide

<400> SEQUENCE: 12

Asn Arg Pro Arg Phe Leu Phe Xaa Xaa
1               5

<210> SEQ ID NO 13
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (8)..(8)
<223> OTHER INFORMATION: Xaa is aminoisobutyric acid (Aib)
<220> FEATURE:
<221> NAME/KEY: MISC_FEATURE
<222> LOCATION: (9)..(9)
<223> OTHER INFORMATION: Xaa is 6-Aminohexanoic acid (Ahx)
<220> FEATURE:
<221> NAME/KEY: MISC_FEATURE
<222> LOCATION: (10)..(10)
<223> OTHER INFORMATION: Xaa is N-terminal iminodiacetic acid mono-N-
    palmityl amide

<400> SEQUENCE: 13

Asn Arg Pro Arg Phe Leu Phe Xaa Xaa Xaa
1               5                   10

<210> SEQ ID NO 14
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is
    40-Amino-4,7,10,13,16,19,22,25,28,31,34,37-dodecaoxotetradecanoic
    acid
<220> FEATURE:
<221> NAME/KEY: MISC_FEATURE
<222> LOCATION: (2)..(2)
<223> OTHER INFORMATION: Xaa is Aminoisobutyric acid (Aib)

<400> SEQUENCE: 14

Xaa Xaa Phe Leu Phe Arg Pro Arg Asn
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is N-terminal iminodiacetic acid mono-N-
      palmityl amide
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 15

Xaa Xaa Phe Leu Phe Arg Pro Arg Asn
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is modified with alkyl chain C16
<220> FEATURE:
<221> NAME/KEY: MISC_FEATURE
<222> LOCATION: (1)..(1)
<223> OTHER INFORMATION: Xaa is N-terminal iminodiacetic acid mono-N-
      palmityl amide
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 16

Xaa Xaa Phe Leu Phe Arg Pro Arg Asn
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is modified with nicotinamide
<220> FEATURE:
<221> NAME/KEY: MISC_FEATURE
<222> LOCATION: (1)..(1)
<223> OTHER INFORMATION: Xaa is N-terminal iminodiacetic acid mono-N-
      palmityl amide
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 17

Xaa Xaa Phe Leu Phe Arg Pro Arg Asn
1               5

<210> SEQ ID NO 18

```
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is modified with alkyl chain (C16)2
<220> FEATURE:
<221> NAME/KEY: MISC_FEATURE
<222> LOCATION: (1)..(1)
<223> OTHER INFORMATION: Xaa is 6-Aminohexanoic acid (Ahx)
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 18

Xaa Xaa Phe Leu Phe Arg Pro Arg Asn
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (9)..(9)
<223> OTHER INFORMATION: Xaa is aminoisobutyric acid (Aib)

<400> SEQUENCE: 19

Xaa Phe Leu Phe Arg Pro Arg Asn Xaa
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Xaa is aminoisobutyric acid (Aib)
<220> FEATURE:
<221> NAME/KEY: MISC_FEATURE
<222> LOCATION: (9)..(9)
<223> OTHER INFORMATION: Xaa is aminoisobutyric acid (Aib)

<400> SEQUENCE: 20

Xaa Phe Leu Phe Arg Pro Arg Asn Xaa
1               5

<210> SEQ ID NO 21
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
```

```
<223> OTHER INFORMATION: Xaa is
      40-Amino-4,7,10,13,16,19,22,25,28,31,34,37-dodecaoxotetradecanoic
      acid
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (10)..(10)
<223> OTHER INFORMATION: Xaa is aminoisobutyric acid (Aib)

<400> SEQUENCE: 21

Xaa Xaa Phe Leu Phe Arg Pro Arg Asn Xaa
1               5                   10

<210> SEQ ID NO 22
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 22

Cys Xaa Phe Leu Phe Arg Pro Arg Asn Xaa Cys
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (7)..(7)
<223> OTHER INFORMATION: Xaa is 2-Carboxyoctahydroindole (Oic)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 23

Cys Xaa Phe Leu Phe Arg Xaa Arg Asn Xaa Cys
1               5                   10

<210> SEQ ID NO 24
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
```

```
<221> NAME/KEY: MISC_FEATURE
<222> LOCATION: (7)..(7)
<223> OTHER INFORMATION: Xaa is 3-Carboxyisoquinoline (Tic)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 24

Cys Xaa Phe Leu Phe Arg Xaa Arg Asn Xaa Cys
1               5                   10

<210> SEQ ID NO 25
<211> LENGTH: 11
<212> TYPE: PRT
<213> ORGANISM: Artificial sequence
<220> FEATURE:
<223> OTHER INFORMATION: Cyclic analog of NM8 modified with
     1,3-bis(Methyl-S-cysteinyl)-benzene
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 25

Cys Xaa Phe Leu Phe Arg Pro Arg Asn Xaa Cys
1               5                   10

<210> SEQ ID NO 26
<211> LENGTH: 11
<212> TYPE: PRT
<213> ORGANISM: Artificial sequence
<220> FEATURE:
<223> OTHER INFORMATION: Cyclic analog of NM9 modified with
     1,3-bis(Methyl-S-cysteinyl)-benzene
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (7)..(7)
<223> OTHER INFORMATION: Xaa is 2-Carboxyoctahydroindole (Oic)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 26

Cys Xaa Phe Leu Phe Arg Xaa Arg Asn Xaa Cys
1               5                   10

<210> SEQ ID NO 27
<211> LENGTH: 11
<212> TYPE: PRT
<213> ORGANISM: Artificial sequence
<220> FEATURE:
<223> OTHER INFORMATION: Cyclic analog of NM10 modified with
     1,3-bis(Methyl-S-cysteinyl)-benzene
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (7)..(7)
<223> OTHER INFORMATION: Xaa is 3-Carboxyisoquinoline (Tic)
<220> FEATURE:
<221> NAME/KEY: MISC_FEATURE
```

```
<222> LOCATION: (10)..(10)
<223> OTHER INFORMATION: Xaa is 6-Aminohexanoic acid (Ahx)

<400> SEQUENCE: 27

Cys Xaa Phe Leu Phe Arg Xaa Arg Asn Xaa Cys
1               5                   10

<210> SEQ ID NO 28
<211> LENGTH: 11
<212> TYPE: PRT
<213> ORGANISM: Artificial sequence
<220> FEATURE:
<223> OTHER INFORMATION: Cyclic analog of NM8 modified with
      3,5-bis(Methyl-S-cysteinyl)-1-(methyl-S-palmityl)-benzene
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 28

Cys Xaa Phe Leu Phe Arg Pro Arg Asn Xaa Cys
1               5                   10

<210> SEQ ID NO 29
<211> LENGTH: 11
<212> TYPE: PRT
<213> ORGANISM: Artificial sequence
<220> FEATURE:
<223> OTHER INFORMATION: Cyclic analog of NM9 modified with
      3,5-bis(Methyl-S-cysteinyl)-1-(methyl-S-palmityl)-benzene
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (7)..(7)
<223> OTHER INFORMATION: Xaa is 2-Carboxyoctahydroindole (Oic)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 29

Cys Xaa Phe Leu Phe Arg Xaa Arg Asn Xaa Cys
1               5                   10

<210> SEQ ID NO 30
<211> LENGTH: 11
<212> TYPE: PRT
<213> ORGANISM: Artificial sequence
<220> FEATURE:
<223> OTHER INFORMATION: Cyclic analog of NM10 modified with
      3,5-bis(Methyl-S-cysteinyl)-1-(methyl-S-palmityl)-benzene
<220> FEATURE:
<221> NAME/KEY: MISC_FEATURE
<222> LOCATION: (2)..(2)
<223> OTHER INFORMATION: Xaa is 6-Aminohexanoic acid (Ahx)
<220> FEATURE:
<221> NAME/KEY: MISC_FEATURE
<222> LOCATION: (7)..(7)
<223> OTHER INFORMATION: Xaa is 3-Carboxyisoquinoline (Tic)
<220> FEATURE:
<221> NAME/KEY: MISC_FEATURE
<222> LOCATION: (10)..(10)
<223> OTHER INFORMATION: Xaa is 6-Aminohexanoic acid (Ahx)

<400> SEQUENCE: 30
```

```
Cys Xaa Phe Leu Phe Arg Xaa Arg Asn Xaa Cys
1               5                   10
```

<210> SEQ ID NO 31
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 31

```
Phe Leu Phe Arg Pro Arg Asn
1               5
```